(12) United States Patent
Reichelt et al.

(10) Patent No.: US 12,404,273 B2
(45) Date of Patent: Sep. 2, 2025

(54) CRYSTAL FORM OF AN ORGANIC FLUORESCENT COMPOUND

(71) Applicant: BASF SE, Ludwigshafen am Rhein (DE)

(72) Inventors: Helmut Reichelt, Ludwigshafen am Rhein (DE); Christian Doerr, Ludwigshafen am Rhein (DE); Gerd Rollar, Frankenthal (DE); Hans Reichert, Basel (CH); Oliver Seeger, Ludwigshafen am Rhein (DE); Korinna Dormann, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 853 days.

(21) Appl. No.: 17/633,989

(22) PCT Filed: Aug. 13, 2020

(86) PCT No.: PCT/EP2020/072726
§ 371 (c)(1),
(2) Date: Feb. 9, 2022

(87) PCT Pub. No.: WO2021/037575
PCT Pub. Date: Mar. 4, 2021

(65) Prior Publication Data
US 2022/0332715 A1   Oct. 20, 2022

(30) Foreign Application Priority Data
Aug. 23, 2019  (EP) .................................... 19193317

(51) Int. Cl.
C07D 471/06    (2006.01)
B41M 3/14      (2006.01)
C09D 11/037    (2014.01)
C09D 11/10     (2014.01)
C09D 11/50     (2014.01)

(52) U.S. Cl.
CPC ........... *C07D 471/06* (2013.01); *B41M 3/144* (2013.01); *C09D 11/037* (2013.01); *C09D 11/10* (2013.01); *C09D 11/50* (2013.01); *C07B 2200/13* (2013.01)

(58) Field of Classification Search
CPC .................................................. C07D 471/06
See application file for complete search history.

(56) References Cited

U.S. PATENT DOCUMENTS

2008/0241492 A1   10/2008   Demartin et al.

FOREIGN PATENT DOCUMENTS

| DE | 3545004 A1 | 6/1987 |
| DE | 102006020190 A1 | 11/2007 |
| WO | 2017/121833 A1 | 7/2017 |

OTHER PUBLICATIONS

International Search Report and Written Opinion received for PCT Patent Application No. PCT/EP2020/072726, mailed on Oct. 16, 2020, 7 pages.

*Primary Examiner* — Paul V Ward
(74) *Attorney, Agent, or Firm* — Faegre Drinker Biddle & Reath LLP

(57) ABSTRACT

The present invention relates to a new crystal form of the compound of formula and a process for its preparation. The compound may be used in compositions for inks, paints and plastics, especially in a wide variety of printing systems and is particularly well-suited for security applications.

(I)

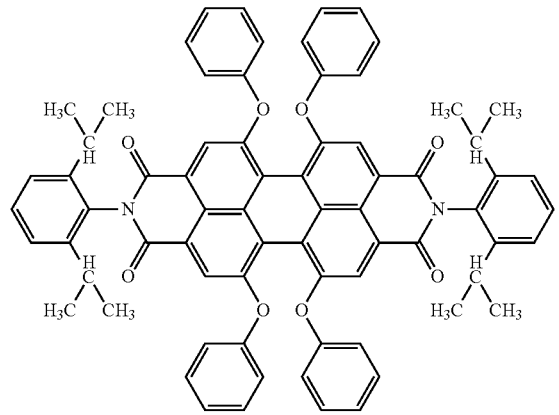

12 Claims, 2 Drawing Sheets

X-ray diffraction (PXRD) pattern of Form A of compound (1) described in DE3545004A1

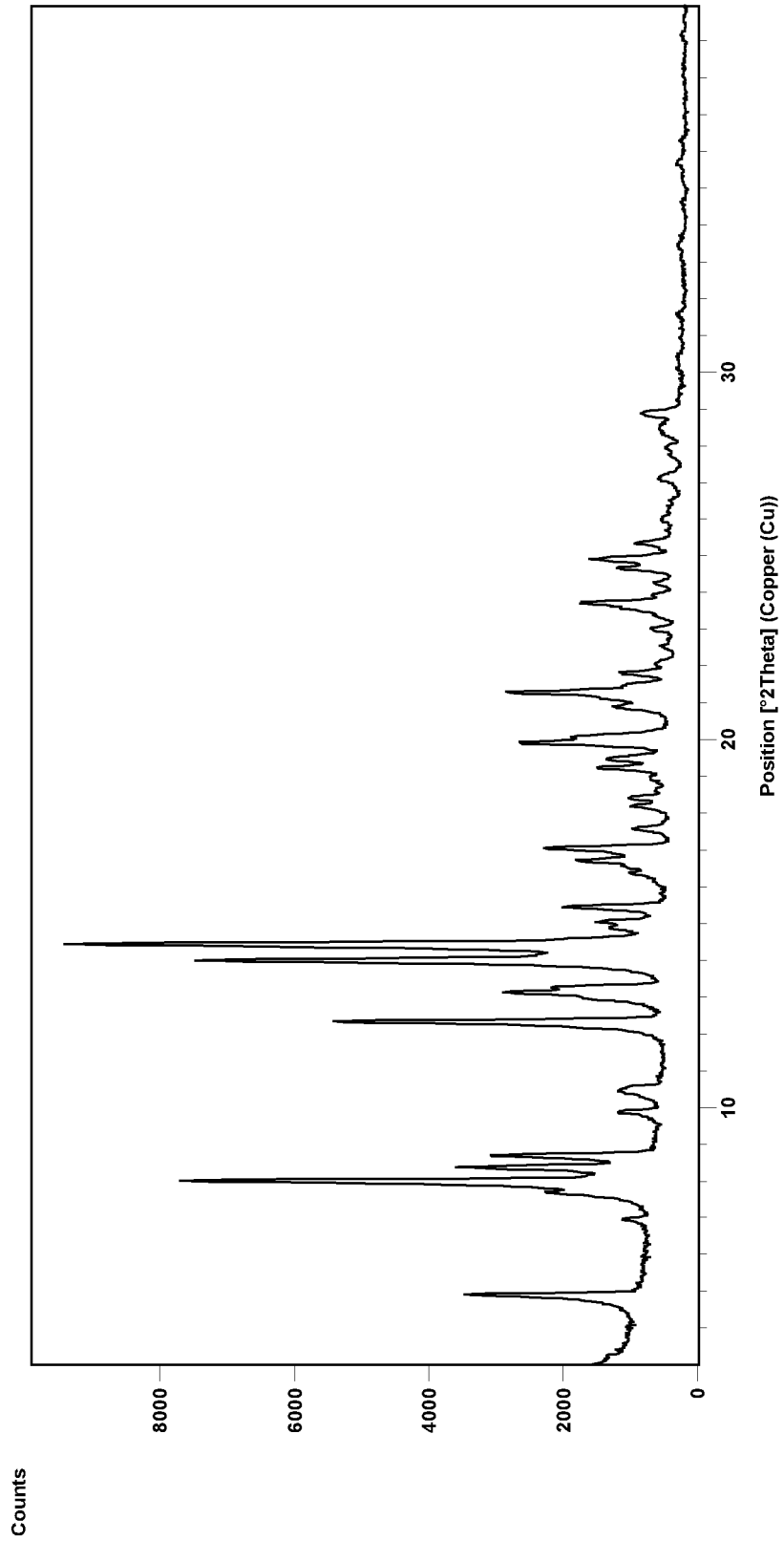

CRYSTAL FORM OF AN ORGANIC FLUORESCENT COMPOUND

CROSS-REFERENCE TO RELATED APPLICATIONS

This application is a national stage application (under 35 U.S.C. § 371) of PCT/EP2020/072726, filed Aug. 13, 2020, which claims benefit of European Application No. 19193317.5, filed Aug. 23, 2019, both of which are incorporated herein by reference in their entirety.

The present invention relates to a new crystal form of a fluorescent compound and a process for its preparation. The compound may be used in compositions for inks, paints and plastics, especially in a wide variety of printing systems and is particularly well-suited for security applications.

WO2017/121833 relates to perylene bisimides with rigid 2,2'-biphenoxy bridges which can be used in color converters for improving the luminous efficacy of LEDs and in printing ink formulations for security printing.

DE102006020190 describes nano-dispersions of perylene dyes in water, which can be used, for example, as vat dyes or mordant dyes, as nano-pigments for ink, paint and plastics, for marking and testing applications and for tracer applications in medicine.

In Example 2 of DE3545004A1 the synthesis of the compound of formula

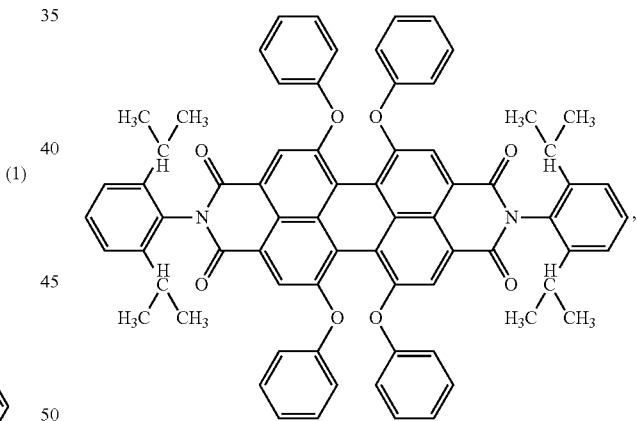

(1)

(Form A of compound (1)) is described.

A new crystal form of the compound of formula

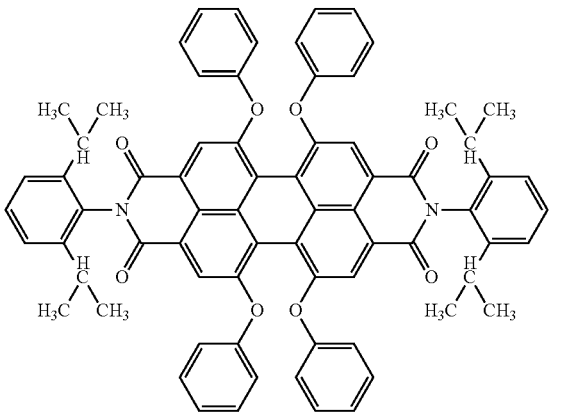

(1)

(Form B of compound (1)) has been found, surprisingly, which is thermally more stable than Form A of compound (1) described in DE3545004A1. The new crystal form of compound (1) exhibits high resistance against chemicals and solvents without losing their other advantages like good light stability and good thermal stability. They can be advantageously employed as fluorescent compound for security printing, especially for bank notes.

In a first aspect, the invention provides a new crystal form of (compound (1))

characterized in an X-ray diffraction pattern by diffraction peaks corresponding to two theta scattering angles of 8.0; 12.3; 14.0 and 21.3.

The x-ray diffraction patterns are measured with Cu—$K_{alpha}$ radiation. It will be understood that the d-value and the scattering angle (two theta) are, of course, subject to fluctuation due to experimental error of +/−0.2 (scattering angle).

The new crystal form of compound (1) is more stable than a crystal form of compound (1) (Form A of compound (1)) which is characterized in an X-ray diffraction pattern by diffraction peaks corresponding to two theta scattering angles of 9.2; 11.1; 13.3 and 14.9.

In a further aspect, the invention provides a printing ink formulation for security printing, comprising the new crystal form of compound (1) as defined above and in the following.

In a further aspect, the invention provides a security document, comprising a substrate and the new crystal form of compound (1) as defined above and in the following.

In a further aspect, the invention provides a security document, obtainable by a printing process, wherein a printing ink formulation is employed that comprises the new crystal form of compound (1) as defined above and in the following.

BRIEF DESCRIPTION OF FIGURES

FIG. 2 depicts the PXRD pattern of Form B of Compound (1) according to the present invention.

Figure 1:
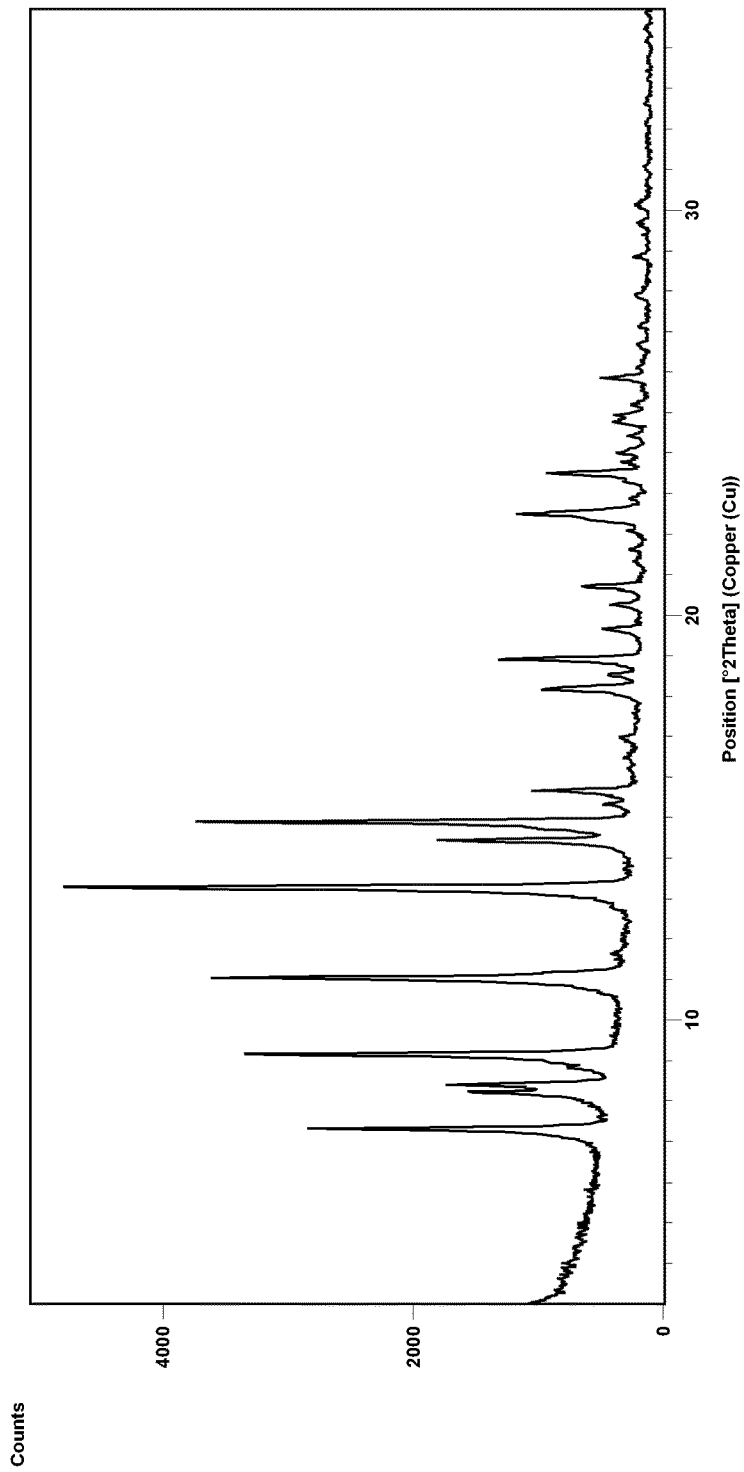
FIG. 1 shows the powder X-ray diffraction (PXRD) pattern of Form A of compound (1) described in DE3545004A1.

The new crystal form of compound (1) is characterized by the PXRD pattern shown in FIG. 2.

In general, the compound (1) has at least one of the following advantageous properties:
  high molar extinction coefficient,
  high fluorescence quantum yield,
  good fastness to chemicals, in particular fastness to bleaching with hypochlorite and fastness to solvents (like toluene, acetone or dichloromethane),
  good fastness to boiling water,
  good fastness to light,
  good heat stability,
  high compatibility with a multiplicity of formulations, in particular printing ink formulations used in security printing.

The new crystal form of compound (1) (Form B of compound (1)) is thermally more stable than Form A of compound (1) described in DE3545004A1. As shown in Example 1 of the present application Form B of compound (1) is the thermodynamic stable form and, hence, is characterized by improved process stability (no problem for higher temperature handling), processability, reproducibility and storage stability in comparison to Form A of compound (1). In addition, Form B of compound (1) has a higher degree of order, because it has 4 molecules per unit cell, whereas Form A of compound (1) has 6 molecules per unit cell.

The new crystal form of the compound of formula (1) according to the present invention can be produced by heating a crystal form of the compound of formula (1), which is characterized in an X-ray diffraction pattern by diffraction peaks corresponding to two theta scattering angles 9.2; 11.1; 13.3 and 14.9 at elevated temperature for 5 minutes to 12 hours.

If dimethylformamide is used as solvent, the mixture is refluxed for 1 to 10 hours at 100 to 120° C., solids are precipitated by adding acetic acid and are purified by recrystallisation in glacial acetic acid and washing with acetic acid, ethanol and water. Reference is made to Example 1 of the present application.

The new crystal form of compound (1), or the new crystal form of compound (1) obtained according to the process described above, or below, can be used inter alia in security printing, for colouring coatings, printing inks and plastics, for data storage, for optical labels, for security labels in documents and for brand protection, for solar collectors, for optical waveguides, as wavelength conversion material for agriculture, or as a fluorescent label for biomolecules.

The new crystal form of compound (1) can also be used in the form of a mixture, comprising new crystal form of compound (1) and at least one further fluorescent compound different from the new crystal form of compound (1). Suitable further fluorescent compounds are in principle all known classes of fluorescent compounds that are compatible with the new crystal form of compound (1). Suitable further fluorescent compounds are e.g. coumarins, stilbenes, benzoxazoles, indanthrenes, benzthiazoles, benzdiazoles, bipyridyl derivatives, rare earth metal complex compounds, colourless inorganic fluorescent materials as well as daylight fluorescent organic materials, e.g. perylenes, xanthenes, acridines, maleimides, naphtalimides, Pigment Yellow 101 (=2,2'-dihydroxynaphtaldazine (Lumogen® Gelb S 0790)), Irgazin Gelb GF (1,2,3,4-tetrachloro-benzo[4,5]imidazo[2,1-a]isoindol-11-one).

The new crystal form of compound (1) can be generally used in a concentration of from 10 ppm to 25%, preferably 100 ppm to 10%, depending on the chosen application.

The present invention is also directed to plastic materials comprising the fluorescent new crystal form of compound (1), or the new crystal form of compound (1) obtained according to the process described above, or below. Preferably, the plastic material comprises at least one thermoplastic polymer. Preferably, the thermoplastic polymer is selected from
  homo- and copolymers which comprise at least one copolymerized monomer selected from $C_2$-$C_{10}$-monoolefins, 1,3-butadiene, 2-chloro-1,3-butadiene, vinyl alcohol and its $C_2$-$C_{10}$-alkyl esters, vinyl chloride, vinylidene chloride, glycidyl acrylate, glycidyl methacrylate, acrylates and methacrylates of $C_1$-$C_{10}$-alcohols, vinylaromatics, (meth)acrylonitrile, maleic anhydride, and ethylenically unsaturated mono- and dicarboxylic acids,
  homo- and copolymers of vinyl acetals,
  polyvinyl esters,
  polyvinylchlorides
  polycarbonates,
  polyesters,
  polyethers,
  polyether ketones,
  thermoplastic polyurethanes,
  polysulfides,
  polysulfones,
  polyether sulfones,
  cellulose alkyl esters,
  polypropylenes
  polyethylene terephthalates
and mixtures of two or more thereof.

Mention may be made by way of example of polyacrylates having identical or different alcohol moieties from the group of the C4-C8-alcohols (particularly of butanol, hexanol, octanol, and 2-ethylhexanol), polycarbonate, polymethyl methacrylate (PMMA), methyl methacrylate, butyl acrylate copolymers, acrylonitrile-butadiene-styrene copolymers (ABSs), ethylene-propylene copolymers, ethylene-propylene-diene copolymers (EPDMs), polystyrene (PS), styrene-acrylonitrile copolymers (SANs), acrylonitrile-styrene-acrylate (ASA), styrene-butadiene-methyl methacrylate copolymers (SBMMAs), styrene-maleic anhydride copolymers, styrene-methacrylic acid copolymers (SMAs), polyoxymethylene (POM), polyvinyl alcohol (PVAL), polyvinyl acetate (PVA), polyvinylbutyral (PVB), polycaprolactone (PCL), polyhydroxybutyric acid (PHB), polyhydroxyvaleric acid (PHV), polylactic acid (PLA), ethylcellulose (EC), cellulose acetate (CA), cellulose propionate (CP), and cellulose acetate/butyrate (CAB).

Preferably, the plastic material comprises, in particular consists of, a polymer selected from the group consisting of polyester, polycarbonate (PC), polystyrene (PS), polymethyl methacrylate (PMMA), polyvinylchloride, polyamide, polyethylene, polypropylene, styrene/acrylonitrile (SAN), acrylonitrile/butadiene/styrene (ABS) and mixtures of two or more thereof. Particular preference is given to polycarbonate, polyester, or poly(methyl-methacrylate).

The plastic material may further comprise suitable stabilizers to stabilize the polymer. Such stabilizers are known to the skilled person and include antioxidants, UV absorbers, light stabilizers, hindered amine light stabilizers, antiozonants and the like, in particular hindered amine light stabilizers. The term "hindered amine light stabilizer" refers to sterically hindered amines of the class of compounds typically represented by 2,2,6,6 tetraalkyl piperidines.

In case the plastic material comprises a stabilizer, the matrix material preferably comprises the stabilizer in an amount of 0.001% by weight to 10% by weight, based on the total weight of the sum of all plastic materials.

According to one preferred embodiment, the plastic material consists of the polymeric material.

Security printing is the field that deals with the printing of items such as currency, passports, tamper-evident labels, stock certificates, postage stamps, identity cards, etc. The main goal of security printing is to prevent forgery, tampering or counterfeiting.

In the field of automated banknote processing, fluorescence plays an important role. Most of the actually circulating currency carries not only visibly coloured printings, but also specific features which are only detectable by irradiation with UV light. Generally, these fluorescent features are implemented for use by automatic currency processing equipment, in banking and vending applications (automatic teller machines, automatic vending machines, etc.), in order to recognize a determined currency bill and to verify its authenticity, in particular to discriminate it from replicas made by colour copiers.

All security documents are required to have good stability and durability. In the case of bank notes, these requirements are extreme, as bank notes are subjected to toughest use conditions by the public—they are subjected to material stress by folding, crumpling etc., subjected to abrasion, exposed to weather, exposed to bodily fluids such as perspiration, laundered, dry-cleaned, ironed etc.—and, after having been subjected to this, are expected to be as legible as when they started. Furthermore, it is essential that the documents nevertheless should have a reasonable life time, ideally of some years, despite suffering the afore-mentioned conditions. During this time, the documents, and thus the inks on them (including invisible security markings), should be resistant to fading or colour change. Hence, any ink used in a security printing process should, when cured, be robust, water-resistant, resistant to various chemicals and flexible. Moreover, as certain states are moving away from the use of paper as the substrate for bank notes, the employed printing ink formulations should be useable on plastics as well as paper. The new crystal form of compound (1) because of their unique application properties is especially suitable for printing ink formulations that are employed for security printing and in particular for bank notes.

In security printing, new crystal form of compound (1) is added to a printing ink formulation. Suitable printing inks are water-based, oil-based or solvent-based printing inks, based on pigment or dye, for inkjet printing, flexographic printing, screen printing, intaglio printing, offset printing, laser printing or letterpress printing and for use in electrophotography. Printing inks for these printing processes usually comprise solvents, binders, and also various additives, such as plasticizers, antistatic agents or waxes. Printing inks for offset printing and letterpress printing are usually formulated as high-viscosity paste printing inks, whereas printing inks for flexographic printing and intaglio printing are usually formulated as liquid printing inks with comparatively low viscosity.

In the context of the present invention, the expression "printing ink" also encompasses formulations that in addition to the new crystal form of compound (1) comprise a colorant. The expression "printing ink" also encompasses printing lacquers that comprise no colorant.

The printing ink formulation for security printing according to the invention preferably comprises
a) new crystal form of compound (1) as defined above, or the new crystal form of compound (1) obtained according to the process described above, or below,
b) a polymeric binder,
c) a solvent,
d) optionally at least one colorant, and
e) optionally at least one further additive.

Suitable components of printing inks are conventional and are well known to those skilled in the art. Examples of such components are described in "Printing Ink Manual", fourth edition, Leach R. H. et al. (eds.), Van Nostrand Reinhold, Wokingham, (1988). Details of printing inks and their formulation are also disclosed in "Printing Inks"-Ullmann's Encyclopedia of Industrial Chemistry, Sixth Edition, 1999 Electronic Release.

A formulation of an IR-absorbing intaglio ink formulation is described in US20080241492A1. The disclosure of the afore-mentioned documents is incorporated herein by reference.

The printing ink formulation according to the invention contains in general from 0.0001 to 25% by weight, preferably from 0.001 to 5% by weight, in particular from 0.01 to 0.1% by weight, based on the total weight of the printing ink formulation, of component a).

The new crystal form of compound (1) is present in the printing ink formulation in dissolved form or in solid form (in a finely dispersed state).

The printing ink formulation according to the invention contains in general from 5 to 74% by weight, preferably from 10 to 60% by weight, more preferably from 15 to 40% by weight, based on the total weight of the printing ink formulation, of component b).

Suitable polymeric binders b) for the printing ink formulation according to the invention are for example selected from natural resins, phenol resin, phenol-modified resins, alkyd resins, polystyrene homo- and copolymers, terpene resins, silicone resins, polyurethane resins, urea-formaldehyde resins, melamine resins, polyamide resins, polyacrylates, polymethacrylates, chlorinated rubber, vinyl ester resins, acrylic resins, epoxy resins, nitrocellulose, hydrocarbon resins, cellulose acetate, and mixtures thereof.

The printing ink formulation according to the invention can also comprise components that form a polymeric binder by a curing process. Thus, the printing ink formulation according to the invention can also be formulated to be energy-curable, e.g. able to be cured by UV light or EB (electron beam) radiation. In this embodiment, the binder comprises one or more curable monomers and/or oligomers. Corresponding formulations are known in the art and can be found in standard textbooks such as the series "Chemistry & Technology of UV & EB Formulation for Coatings, Inks & Paints", published in 7 volumes in 1997-1998 by John Wiley & Sons in association with SITA Technology Limited.

Suitable monomers and oligomers (also referred to as prepolymers) include epoxy acrylates, acrylated oils, urethane acrylates, polyester acrylates, silicone acrylates, acrylated amines, and acrylic saturated resins. Further details and examples are given in "Chemistry & Technology of UV & EB Formulation for Coatings, Inks & Paints", Volume II: Prepolymers & Reactive Diluents, edited by G Webster.

If a curable polymeric binder is employed, it may contain reactive diluents, i.e. monomers which act as a solvent and which upon curing are incorporated into the polymeric binder. Reactive monomers are typically chosen from acrylates or methacrylates, and can be monofunctional or multifunctional. Examples of multifunctional monomers include polyester acrylates or methacrylates, polyol acrylates or methacrylates, and polyether acrylates or methacrylates.

In the case of printing ink formulations to be cured by UV radiation, it is usually necessary to include at least one photoinitiator to initiate the curing reaction of the monomers upon exposure to UV radiation. Examples of useful photoinitiators can be found in standard textbooks such as "Chemistry & Technology of UV & EB Formulation for Coatings, Inks & Paints", Volume III, "Photoinitiators for Free Radical Cationic and Anionic Polymerisation", 2nd edition, by J. V. Crivello & K. Dietliker, edited by J. Bradley and published in 1998 by John Wiley & Sons in association with SITA Technology Limited. It may also be advantageous to include a sensitizer in conjunction with the photoinitiator in order to achieve efficient curing.

The printing ink formulation according to the invention contains in general from 1 to 94.9999% by weight, preferably from 5 to 90% by weight, in particular from 10 to 85% by weight, based on the total weight of the printing ink formulation, of a solvent c).

Suitable solvents are selected from water, organic solvents and mixtures thereof. For the purpose of the invention, reactive monomers which also act as solvent are regarded as part of the afore-mentioned binder component b).

Examples of solvents comprise water; alcohols, e.g. ethanol, 1-propanol, 2-propanol, ethylene glycol, propylene glycol, diethylene glycol and ethoxy propanol; esters, e.g. ethyl acetate, isopropyl acetate, n-propyl acetate and n-butyl acetate; hydrocarbons, e.g. toluene, xylene, mineral oils and vegetable oils, and mixtures thereof.

The printing ink formulation according to the invention may contain an additional colorant d). Preferably, the printing ink formulation contains in from 0 to 25% by weight, more preferably from 0.1 to 20% by weight, in particular from 1 to 15% by weight, based on the total weight of the printing ink formulation, of a colorant d).

Suitable colorants d) are selected conventional dyes, and in particular conventional pigments. The term "pigment" is used in the context of this invention comprehensively to identify all pigments and fillers, examples being colour pigments, white pigments, and inorganic fillers. These include inorganic white pigments such as titanium dioxide, preferably in the rutile form, barium sulfate, zinc oxide, zinc sulfide, basic lead carbonate, antimony trioxide, lithopones (zinc sulfide+barium sulfate), or colored pigments, examples being iron oxides, carbon black, graphite, zinc yellow, zinc green, ultramarine, manganese black, antimony black, manganese violet, Paris blue or Schweinfurt green. Besides the inorganic pigments the printing ink formulation of the invention may also comprise organic colour pigments, examples being sepia, gamboge, Cassel brown, toluidine red, para red, Hansa yellow, indigo, azo dyes, anthraquinonoid and indigoid dyes, and also azo, dioxazine, quinacridone, perylene, quinophthalone, diketopyrrolopyrrole, phthalocyanine, isoindoline, isoindolinone, and metal complex pigments. Also suitable are synthetic white pigments with air inclusions to increase the light scattering, such as the Rhopaque® dispersions. Suitable fillers are, for example, aluminosilicates, such as feldspars, silicates, such as kaolin, talc, mica, magnesite, alkaline earth metal carbonates, such as calcium carbonate, in the form for example of calcite or chalk, magnesium carbonate, dolomite, alkaline earth metal sulfates, such as calcium sulfate, silicon dioxide, etc.

The printing ink formulation according to the invention may contain at least one additive e). Preferably, the printing ink formulation contains in from 0 to 25% by weight, more preferably from 0.1 to 20% by weight, in particular from 1 to 15% by weight, based on the total weight of the printing ink formulation, of at least one component e).

Suitable additives (component e) are selected from plasticizers, waxes, siccatives, antistatic agents, chelators, antioxidants, stabilizers, adhesion promoters, surfactants, flow control agents, defoamers, biocides, thickeners, etc. and combinations thereof. These additives serve in particular for fine adjustment of the application-related properties of the printing ink, examples being adhesion, abrasion resistance, drying rate, or slip.

In particular, the printing ink formulation for security printing according to the invention preferably contains
a) 0.0001 to 25% by weight of new crystal form of compound (1), or the new crystal form of compound (1) obtained according to the process described above, or below,
b) 5 to 74% by weight of at least one polymeric binder,
c) 1 to 94.9999% by weight of at least one a solvent,
d) 0 to 25% by weight of at least one colorant, and
e) 0 to 25% by weight of at least one further additive,
wherein the sum of components a) to e) adds up to 100%.

The printing ink formulations according to the invention are advantageously prepared in a conventional manner, for example by mixing the individual components. As mentioned earlier, new crystal form of compound (1) is present in the printing ink formulations in a (partly) dissolved or finely dispersed solid form. Additional colorants may be employed in the printing ink formulation of the invention or in a separate ink formulation. When additional colorants are to be employed in a separate formulation, the time of application of the printing ink formulation according to the invention is usually immaterial. The printing ink formulation according to the invention can for example be applied first and then be overprinted with conventional printing inks. But it is also possible to reverse this sequence or, alternatively, to apply the printing ink formulation according to the invention in a mixture with conventional printing inks. In every case the prints are readable with suitable light sources.

Primers can be applied prior to the printing ink formulation according to the invention. By way of example, the primers are applied in order to improve adhesion to the substrate. It is also possible to apply additional printing lacquers, e.g. in the form of a covering to protect the printed image. Additional printing lacquers may also be applied to serve aesthetic purposes, or serve to control application-related properties. By way of example, suitably formulated additional printing lacquers can be used to influence the roughness of the surface of the substrate, the electrical properties, or the water-vapour-condensation properties. Printing lacquers are usually applied in-line by means of a lacquering system on the printing machine employed for printing the printing ink formulation according to the invention.

The printing ink formulations according to the invention are also suitable for use in multilayer materials. Multilayer materials are e.g. composed of two or more plastics foils, such as polyolefin foils, metal foils, or metallised plastics foils, which are bonded to one another, by way of example, via lamination or with the aid of suitable laminating adhesives. These composites may also comprise other functional layers, such as odour-barrier layers or water-vapour barriers.

The following examples illustrate the invention without restricting it.

EXAMPLES

X-Ray Powder Diffraction Method:

Conditions for obtaining powder X-ray diffraction (XRD) patterns: The powder x-ray diffraction patterns were obtained by methods known in the art using PANanalytical X-pert Pro diffractometer with X'Celerator detector using CuK α radiation (tube operating at 45 kV and 40 mA) in the Bragg-Brentano (reflection) geometry. Data were recorded from 3.006 to 35.006° 2 θ in steps of 0.0167113° 2 θ and the measurement time of 19.050 seconds per step. Variable divergence and antiscatter slits were used to maintain 5 mm of sample length irradiated.

Comparative Example 1

Preparation of Form A of Compound (1):

The compound is known from DE3545004A1 and its preparation is described in Example 2 of DE3545004A1. The obtained product (crystals) shows the PXRD pattern of Form A of compound (1). Reference is made to FIG. 1.

Example 1

100 g of the solids of compound (1) obtained in Comparative Example 1 (Form A of compound (1)) were suspended in 0.9 l of dimethylformamide. The mixture was stirred for 4 h at 110° C., cooled to room temperature and 0.2 l ethanol was added. For precipitation 0.26 l of 40% acetic acid was added, the precipitate was filtered and washed with 40% acetic acid. The obtained solid was suspended in 0.35 l glacial acetic acid and stirred at 90° C. for 4 h, cooled to room temperature, filtered, washed with 40% acetic acid, ethanol and water at 70° C. and dried, to obtain 75 g of the new crystal form of compound (1) (Form B of compound (1)).

Form B of Compound (1) Characterized by the Following X-Ray Diffraction Pattern:

| Scattering Angle (2 Theta) | d-spacing (Angstrom) | Relative Intensity (%) |
|---|---|---|
| 4.9 ± 0.2 | 17.96014 | 28.91 |
| 8.0 ± 0.2 | 11.03162 | 78.42 |
| 12.3 ± 0.2 | 7.17132 | 54.71 |
| 13.1 ± 0.2 | 6.74129 | 26.63 |
| 14.0 ± 0.2 | 6.32307 | 77.81 |
| 14.4 ± 0.2 | 6.13231 | 100 |
| 15.5 ± 0.2 | 5.73131 | 17.26 |
| 17.1 ± 0.2 | 5.19731 | 20.7 |
| 19.9 ± 0.2 | 4.45561 | 24.99 |
| 21.3 ± 0.2 | 4.17184 | 27.55 |
| 23.7 ± 0.2 | 3.74982 | 15.27 |

Reference is made to FIG. 2.

Application Example 1—UV Ink 0.1 g Form B of compound (1), 100 g Laromer® PE 46T and 3 g diphenyl(2,4,6-trimethylbenzoyl)phosphinoxide (or ethyl(2,4,6-trimethylbenzoyl)phenylphosphinate) were mixed in a speedmixer apparatus in a 60 mL jar. A drawdown was prepared with a 12 (or 24) μm spiral wirebar on PET foil. The coated PET foil was cured 3 times at 120 W/cm$^2$ under a UV belt (Technigraf Aktiprint T/e with Hg-lamp (UT 51072-0004)). The achieved film showed a bright fluorescence.

Instead of Laromer® PE 46T Laromer® EA 9081 (epoxy acrylate), or Laromer® LR 8986 may be used:

Application Example 2—UV Ink 0.1 g Form B of compound (1) was dissolved in 7 g Laromer® DPGDA (dipropylene glycol diacrylate). 3 g Omnirad® 184 was dissolved in 7 g Laromer® DPGDA. Both solutions were added to 83 g Laromer® UA 9048 and mixed either by hand or in a speedmixer equipment. A drawdown with a 24 μm spiral wirebar on a PET film was cured with a Technigraf Aktiprint T/e with Hg-lamp (UT 51072-0004) 3 times at 120 W/cm$^2$ with 20 m/min or 2×40 m/min at 120 W/cm$^2$). The obtained films showed a bright fluorescence.

Instead of Omnirad® 184 Omnirad® 2959 may be used.

Application Example 3—UV Ink 0.125 g Form B of compound (1), 100 g Laromer® UA 9072, 25 g Laromer® DPGDA and 6.25 g diphenyl(2,4,6-trimethylbenzoyl)phosphinoxide were mixed in a Speedmixer DAC 400.1 FVZ in a 60 mL jar with 5 glass beads with a 4 mm diameter for 2*140 minutes. The draw down with 12 μm spiral wirebar on Lumirror 4001/50 μm showed after UV curing (3*120 W/cm$^2$) a strong bright fluorescence.

Instead of Laromer® DPGDA Laromer® LR 8887 may be used. Laromer® UA 9072 may be replaced by Laromer® DPHA (dipentaerythritolhexaacrylate).

Application Example 4—Vinylchloride Copolymer Ink 0.4 g Form B of compound (1) in 39.6 g vinylchloride resin solution (VINNOL E 15/48A 10% in ethyl acetate/methyl ethyl ketone/methyl isobutyl ketone=20:30:47) was dispersed in a 100 mL glass jar with 50 g glass beads with a diameter of 2 mm for 30 minutes in the scandex. With a 24 μm spiral wirebar a drawdown was prepared on acetate film. The film showed a bright fluorescence.

The invention claimed is:

1. A crystal form of a compound of formula (compound (1))

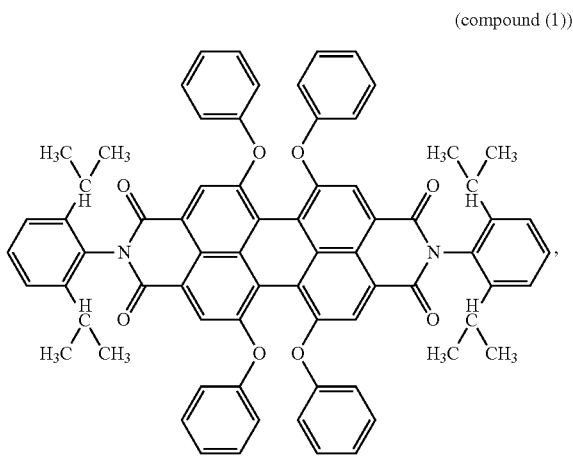 [SMILES: CC(C)c1cccc(C(C)C)c1N1C(=O)c2cc(Oc3ccccc3)c3c4c(Oc5ccccc5)cc5c6c(cc(Oc7ccccc7)c(c7c(Oc8ccccc8)cc(c2c37)C1=O)c64)C(=O)N(c1c(C(C)C)cccc1C(C)C)C5=O]

characterized in an X-ray diffraction pattern by diffraction peaks corresponding to two theta scattering angles of 8.0; 12.3; 14.0 and 21.3.

2. The crystal form of compound (1) according to claim 1, characterized in that it is more stable than a crystal form of the compound of formula (1) which is characterized in an X-ray diffraction pattern by diffraction peaks corresponding to two theta scattering angles of 9.2; 11.1; 13.3 and 14.9.

3. A process for producing the crystal form of compound (1) according to claim 1, which comprises heating a crystal form of compound (1), which is characterized in an X-ray diffraction pattern by diffraction peaks corresponding to two theta scattering angles of 9.2; 11.1; 13.3 and 14.9, in a solvent at reflux for 5 minutes to 12 hours.

4. The process according to claim 3, wherein the solvent is dimethylformamide and the mixture heated at 100 to 120° C. for 1 to 10 hours.

5. The process according to claim 3, wherein after heating of the mixture solids are precipitated by adding acetic acid and are purified by recrystallisation in glacial acetic acid.

6. An article comprising at least one fluorescent film layer, the film layer comprising a polymeric matrix the crystal form of the compound (1) according to claim 1.

7. Printing ink formulation for security printing, comprising
a) the crystal form of compound (1) as defined in claim 1,
b) a polymeric binder,
c) a solvent,
d) optionally at least one colorant, and
e) optionally at least one further additive.

8. Printing ink formulation according to claim 7, comprising
a) 0.0001 to 25% by weight of the crystal form of compound (1),
b) 5 to 74% by weight of at least one polymeric binder,
c) 1 to 94.9999% by weight of at least one a solvent,
d) 0 to 25% by weight of at least one colorant, and
e) 0 to 25% by weight of at least one further additive,
wherein the sum of components a) to e) does not exceed 100%.

9. Security document, comprising a substrate and the crystal form of compound (1) as defined in claim 1.

10. Security document, obtainable by a printing process, wherein the printing ink formulation as defined in claim 7 is employed.

11. Security document according to claim 9, selected from a bank note, a passport, a check, a voucher, an ID- or transaction card, a stamp and a tax label.

12. A method of detecting the authenticity of the security document as defined in claim 9, comprising the steps of:
a) measuring an absorbance, reflectance or transmittance spectrum of the security document in the UV/VIS range of the electromagnetic spectrum; and
b) comparing the spectrum measured under a) and/or information derived therefrom with a corresponding spectrum and/or information of an authentic security element.

* * * * *